US008323570B2

(12) United States Patent
Johnson et al.

(10) Patent No.: US 8,323,570 B2
(45) Date of Patent: Dec. 4, 2012

(54) MICROELECTRONIC SENSOR DEVICE WITH SENSOR ARRAY

(75) Inventors: Mark Thomas Johnson, Eindhoven (NL); Hendrikus Alfonsus Roelof Stapert, Eindhoven (NL); Marc Wilhelmus Gijsbert Ponjee, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 553 days.

(21) Appl. No.: 12/293,573

(22) PCT Filed: Mar. 1, 2007

(86) PCT No.: PCT/IB2007/050665

§ 371 (c)(1), (2), (4) Date: Sep. 19, 2008

(87) PCT Pub. No.: WO2007/107892

PCT Pub. Date: Sep. 27, 2007

(65) Prior Publication Data

US 2010/0229656 A1 Sep. 16, 2010

(30) Foreign Application Priority Data

Mar. 21, 2006 (EP) .................................... 06111438
Mar. 21, 2006 (EP) .................................... 06111439
Mar. 21, 2006 (EP) .................................... 06111442

(51) Int. Cl.
*G01N 33/00* (2006.01)

(52) U.S. Cl. .................................................... 422/82.01

(58) Field of Classification Search ................ 422/82.01
See application file for complete search history.

(56) References Cited

U.S. PATENT DOCUMENTS 4,759,210 A * 7/1988 Wohltjen .................... 73/31.07
5,571,401 A * 11/1996 Lewis et al. .................. 205/787
6,085,576 A * 7/2000 Sunshine et al. ............ 73/29.01
6,255,677 B1 7/2001 Caillat et al.
6,489,106 B1 12/2002 Shivashankar et al.
6,632,400 B1 * 10/2003 Brennen et al. ............ 422/82.01
6,864,140 B2 3/2005 Bryant
6,867,048 B2 3/2005 Kovacs
6,929,731 B2 8/2005 Foret et al.
2001/0000148 A1 4/2001 Kurane et al.
2002/0055119 A1 * 5/2002 Yasuda et al. ..................... 435/6
2004/0043494 A1 3/2004 Amorese et al.
2005/0142036 A1 6/2005 Kim et al.
2005/0196321 A1 9/2005 Huang

FOREIGN PATENT DOCUMENTS

EP 1108472 A2 6/2001
EP 1321520 A1 6/2003

(Continued)

OTHER PUBLICATIONS

HCF4052B; Different 4-Channel Analog Multiplexer/Demultiplexer. STMicroelectronics. Publication Date: Oct. 2002. pp. 1-11.*

(Continued)

*Primary Examiner* — Bobby Ramdhanie

(57) ABSTRACT

The invention relates to different designs of a microelectronic sensor device comprising an array of heating elements (HE) and an array of sensor elements (SE) that are aligned with respect to each other adjacent to a sample chamber (SC). By applying appropriate currents to the heating elements (HE), the sample chamber can be heated according to a desired temperature profile.

20 Claims, 5 Drawing Sheets

FOREIGN PATENT DOCUMENTS

| | | | | |
|---|---|---|---|---|
| WO | 9322678 | A2 | | 11/1993 |
| WO | WO 9908105 | A1 | * | 2/1999 |
| WO | 0202794 | A2 | | 1/2002 |
| WO | 03054523 | A2 | | 7/2003 |
| WO | 03054566 | A1 | | 7/2003 |
| WO | WO 2004074913 | A2 | * | 9/2004 |
| WO | 2005010542 | A2 | | 2/2005 |
| WO | 2005010543 | A1 | | 2/2005 |
| WO | 2005038911 | A1 | | 4/2005 |
| WO | WO 2005118773 | A2 | * | 12/2005 |
| WO | WO 2005124828 | A2 | * | 12/2005 |

OTHER PUBLICATIONS

Akira Yumoto, et al: Pixel-Driving Methods for Large-Sized Poly-Si AM-OLED Displays, Asia Display / IDW '01, Sony Corporation, Core Technology & Network Company, pp. 1395-1398, Publication Date:2001.

R. M. A. Dawson, et al: 24.1 Invited Paper: Pursuit of Active Matrix Light Emitting Diode Displays, 2001 SID Conference Proceeding 24.1, pp. 372-375.

H. Kageyama, et al: 9.1: A 3.5-Inch OLED Display using a 4 TFT Pixel Circuit with an Innovative Pixel Driving Scheme, 2002 SID Conference Proceeding 9.1, pp. 96-99.

* cited by examiner

MICROELECTRONIC SENSOR DEVICE WITH SENSOR ARRAY

FIELD OF THE INVENTION

The invention relates to a microelectronic sensor device with an array of sensor elements for investigating a sample in a sample chamber. Moreover, it relates to the use of such a microelectronic sensor device as a biosensor.

Biosensors often need a well controlled temperature to operate, for example because many biomolecules are only stable in a small temperature window (usually around 37° C.) or become de-activated when temperatures are outside of this temperature window. Temperature regulation is especially of high importance for hybridization assays. In these assays temperature is often used to regulate stringency of the binding of a DNA strand to its complementary strand. A high stringency is required when for instance single point mutations are of interest. Melting temperature ranges (i.e. denaturing of DNA strands) for single point mutation hybridizations can differ only less than 5° C. as compared to the wild types. A control over stringency during hybridization can give extra flexibility to especially multi-parameter testing of DNA hybridization, for example on a DNA micro-array. In these assays one also wants to ramp up temperature in a well controlled way to distinguish between mutations in a multiplexed format.

In the U.S. Pat. No. 6,864,140 B2, some of the aforementioned problems are addressed by local heating elements in the form of a thin film transistor formed on polycrystalline silicon on a substrate adjacent to a sample chamber where (bio-)chemical reactions take place. A further investigation of the sample in the sample chamber is however not possible with this known device. Moreover, the U.S. Pat. No. 6,867,048 B2 discloses a microelectronic biosensor in which a microchip with an array of sensor elements is disposed on a membrane with heating elements. The membrane allows to control the temperature in an adjacent sample chamber in the same way for all sensor elements.

BACKGROUND OF THE INVENTION

From the WO 93/22678, a method and an apparatus are known for identifying molecular structures within a sample using a monolithic array of test sites formed on a substrate. Each test site includes probes for bonding with a predetermined molecular target, wherein said probes have been fixed during the manufacture of the apparatus by selectively heating the test site with a laser beam or with an integrated heating element.

Based on this situation it was an object of the present invention to provide means for a more versatile temperature controlled investigation of a sample in a microelectronic sensor device.

This objective is achieved by a microelectronic sensor device according to claim 1 and a use according to claim 36. Preferred embodiments are disclosed in the dependent claims.

The microelectronic sensor device according to the present invention is intended for the investigation of a sample, particularly a liquid or gaseous chemical substance like a biological body fluid which may contain particles. It comprises the following components:

a) A sample chamber in which the sample to be investigated can be provided. The sample chamber is typically an empty cavity or a cavity filled with some substance like a gel that may absorb a sample substance; it may be an open cavity, a closed cavity, or a cavity connected to other cavities by fluid connection channels.

b) A "sensing array" that comprises a plurality of sensor elements for sensing properties of a sample in the sample chamber, for example the concentration of particular target molecules in a fluid. In the most general sense, the term "array" shall in the context of the present invention denote an arbitrary three-dimensional arrangement of a plurality of elements (e.g. the sensor elements). Typically such an array is two-dimensional and preferably also planar, and the (sensor) elements are arranged in a regular pattern, for example a grid or matrix pattern.

Furthermore, it should be noted that a "heat exchange with a sub-region of the sample chamber" is assumed if such an exchange is strong enough in the sub-region to provoke desired/observable reactions of the sample. This definition shall exclude small "parasitic" thermal effects that are inevitably associated with any active process, e.g. with electrical currents. Typically, a heat flow in the sense of the present invention is larger than 0.01 W/cm$^2$ and will have a duration in excess of 1 millisecond.

c) A "heating array" that comprises a plurality of heating elements for exchanging heat with at least a sub-region of the sample chamber when being driven with electrical energy. The heating elements may preferably convert electrical energy into heat that is transported into the sample chamber. It is however also possible that the heating elements absorb heat from the sample chamber and transfer it to somewhere else under consumption of electrical energy.

d) A control unit for selectively driving the heating elements (i.e. for supplying electrical energy to them) during or prior to the sensing of a sample in the sample chamber.

The aforementioned microelectronic sensor device has the advantage that the sample chamber can at the same time be investigated by the sensor elements and temperature-controlled via the heating elements. This allows to establish optimal temperature conditions in the sample chamber during a measurement, thus improving the accuracy of tests significantly or even making certain tests possible at all.

The control unit is preferably adapted to drive the heating elements such that a desired spatial and/or temporal temperature profile is achieved in the sample chamber. This allows to provide optimal (particularly non-uniform and/or dynamic) conditions for the manipulation of e.g. a sensitive biological sample.

According to a preferred embodiment of the microelectronic sensor device, the heating elements are aligned with respect to the sensor elements. This "alignment" means that there is a fixed (translation-invariant) relation between the positions of the heating elements in the heating array and the sensor elements in the sensing array; the heating and sensor elements may for example be arranged in pairs, or each heating element may be associated with a group of several sensor elements (or vice versa). The alignment has the advantage that the heating and sensor elements interact similarly at different locations. Thus uniform/periodic conditions are provided across the arrays.

A preferred kind of alignment between the sensor and the heating elements is achieved if the patterns of their arrangement in the sensing array and the heating array, respectively, are identical. In this case, each sensor element is associated with just one heating element.

In an alternative embodiment, more than one heating element is associated to each sensor element. This allows to create a spatially non-uniform heating profile, which can result in either a spatially non-uniform or a spatially uniform temperature profile in the region of one sensor element and thus an even better temperature control. Preferably, there is additionally an alignment of the above mentioned kind between heating elements and sensor elements.

The sensing array may for example comprise optical, magnetic, mechanical, acoustic, thermal and/or electrical sensor elements. A microelectronic sensor device with magnetic sensor elements is for example described in the WO 2005/010543 A1 and WO 2005/010542 A2 (which are incorporated into the present text by reference). Said device is used as a microfluidic biosensor for the detection of biological molecules labeled with magnetic beads. It is provided with an array of sensor units comprising wires for the generation of a magnetic field and Giant Magneto Resistance devices (GMRs) for the detection of stray fields generated by magnetized beads. Moreover, optical, mechanical, acoustic, and thermal sensor concepts are described in the WO 93/22678, which is incorporated into the present text by reference.

According to one embodiment of the microelectronic sensor device, the heating array and the sensing array are disposed on opposite sides of the sample chamber. Such an arrangement can readily be combined with known designs of biosensors as only the cover of the sample chamber has to be replaced by the heating array.

In an alternative embodiment, the heating array and the sensing array are disposed on the same side of the sample chamber. In this case, the arrays may be arranged in a layered structure one upon the other, or they may be merged in one layer.

In the aforementioned embodiment with a layered structure, the sensing array is preferably disposed between the sample chamber and the heating array. Thus it will be as close as possible to the sample chamber which guarantees an optimal access to the sample.

The aforementioned arrangements of the heating array relative to the sample chamber and the sensing array can be combined if the heating array comprises two parts which are disposed on different (particularly opposite) sides of the sample chamber. Heating the sample chamber from opposite sides allows to create more uniform temperatures in it as well as to deliberately create temperature gradients directed e.g. from one of the sides to the other.

According to another embodiment of the microelectronic sensor device, the control unit is located outside the array of heating elements and connected to the heating elements by power lines that can selectively carry electrical energy to (or away from) the heating elements. As the amount or rate of transferred electrical energy determines the extent to which heat is exchanged with the sample chamber, the control unit has to allocate the transferred electrical energy appropriately in order to achieve a desired temperature profile in the sample chamber. The heating array can be kept most simple in this approach because the heating elements just have to convert electrical energy into heat without further processing, i.e. they may for example be realized by simple resistors.

In a further development of the aforementioned embodiment, the control unit comprises a de-multiplexer for coupling the control unit to the power lines. This allows to use one circuit for providing several power lines (subsequently) with electrical power.

According to another realization of the microelectronic sensor device, each heating element is associated with a local driving unit, wherein said driving units are geometrically located at (i.e. near) and coupled to the heating elements. Such local driving units can take over certain control tasks and thus relieve the control unit.

In a further development of the aforementioned embodiment, the local driving units are coupled to a common power supply line, and the heating elements are coupled to another common power supply line (e.g. ground). In this case each local driving unit determines the amount of electrical energy or power that is taken from the common power supply lines. This simplifies the design insofar as properly allocated amounts of electrical energy do not have to be transported through the whole array to a certain heating element.

In another embodiment of the microelectronic sensor device with local driving units, a part of the control unit is located outside the array of heating elements and connected via control lines for carrying control signals to the local driving units (which constitute the residual part of the control unit). In this case the outside part of the control unit can determine how much electrical energy or power a certain heating element shall receive; this energy/power needs however not to be transferred directly from the outside control unit to the heating element. Instead, only the associated information has to be transferred via the control signals to the local driving units, which may then extract the needed energy/power e.g. from common power supply lines.

In a preferred realization of the aforementioned embodiment, the control signals are pulse-width modulated (PWM). With such PWM signals, the local driving units can be switched off and on with selectable rate and duty cycle, wherein these parameters determine the average power extraction from common power supply lines. The individual characteristics of the local driving units are then less critical as only an on/off behavior is required.

In a further development of the embodiments with local driving units, said units comprise a memory for storing information of control signals transmitted by the outside part of the control unit. Such a memory may for example be realized by a capacitor that stores the voltage of the control signals. The memory allows to continue a commanded operation of a heating element while the associated control line is disconnected again from the driving unit and used to control other driving units.

In the embodiment with local driving units it often turns out in practice that even with an identical design of the driving units, the components and circuitry that make them up have statistical variations in their characteristics which lead to variations in the behavior of the driving units. Commanding different driving units with the same voltage may then for example lead to different results, e.g. distinct current outputs to the heating elements. This makes a precise control of temperature in the sample chamber difficult if not impossible. The microelectronic sensor device may therefore incorporate means for compensating variations in the individual characteristic values of the driving units. This allows a control with much higher accuracy.

In a typical design of the aforementioned microelectronic sensor device, at least one driving unit comprises a transistor which produces for a given input voltage V at its gate an output current I (which will be fed to the heating element) according to the formula $$I=m\cdot(V-V_{thres})^2,$$

wherein m and $V_{thres}$ are the individual characteristic values of the transistor. The formula illustrates that local driving units with different values of m and $V_{thres}$ will behave differently when controlled with the same voltage.

In the aforementioned case, the driving units preferably each comprise a capacitor coupled to the control gate of said transistor and circuitry to charge this capacitor to a voltage that compensates $V_{thres}$ or that drives the transistor to produce a predetermined current I. Thus the application of a simple capacitor may suffice to compensate individual variations in the very important case of driving units based on a transistor of the kind described above. Further details with respect to an associated circuitry will be described in connection with the Figures.

The heating elements may particularly comprise a resistive strip, a transparent electrode, a Peltier element, a radio frequency heating electrode, or a radiative heating (IR) element. All these elements can convert electrical energy into heat, wherein the Peltier element can additionally absorb heat and thus provide a cooling function.

The microelectronic sensor device may optionally comprise a cooling unit, e.g. a Peltier element or a cooled mass, in thermal contact with the heating array and/or with the sample chamber. This allows to reduce the temperature of the sample chamber if necessary. In combination with a heating array for the generation of heat, a cooling unit therefore enables a complete control of temperature in both directions.

While the heating elements are in most practical cases (only) capable of generating heat, at least one of them may optionally also be adapted to remove heat from the sample chamber. Such a removal may for example be achieved by Peltier elements or by coupling the heating elements to a heat sink (e.g. a mass cooled with a fan).

The microelectronic sensor device may optionally comprise at least one temperature sensor which makes it possible to monitor the temperature in the sample chamber. The temperature sensor(s) may preferably be integrated into the heating array. In a particular embodiment, at least one of the heating elements is designed such that it can be operated as a temperature sensor, which allows to measure temperature without additional hardware.

In cases in which a temperature sensor is available, the control unit is preferably coupled to said temperature sensor and adapted to control the heating elements in a closed loop according to a predetermined (temporal and/or spatial) temperature profile in the sample chamber. This allows to provide robustly optimal conditions for the manipulation of e.g. a sensitive biological sample.

The microelectronic sensor device may further comprise a micromechanical or an electrical device, for example a pump or a valve, for controlling the flow of a fluid and/or the movement of particles in the sample chamber. Controlling the flow of a sample or of particles is a very important capability for a versatile manipulation of samples in a microfluidic device.

In a particular embodiment, at least one of the heating elements may be adapted to create flow in a fluid in the sample chamber by a thermo-capillary effect. Thus its heating capability can be exploited for moving the sample.

If it is necessary or desired to have sub-regions of different temperature in the sample chamber, this may optionally be achieved by dividing the sample chamber with a heat insulation into at least two compartments. Particular embodiments of this approach will be described in more detail in connection with the Figures.

An electrically isolating layer and/or a biocompatible layer may be disposed between the sample chamber and the heating and/or sensing array. Such a layer may for example consist of silicon dioxide $SiO_2$ or the photoresist SU8.

In a further embodiment of the invention, the control unit is adapted to drive the heating elements with an alternating current of selectable intensity and/or frequency. The electrical fields associated with such an operation of the heating elements may in certain cases, for example in cases of di-electrophoresis, generate a motion in the sample if they have an appropriate intensity and frequency. On the other hand, the intensity and frequency of the alternating current determines the average rate of heat production. Thus it is possible to execute a heating and a manipulation function with such a heating element simply by changing the intensity and/or frequency of the applied current appropriately.

The heating element(s) and/or field electrode(s) may preferably be realized in thin film electronics.

When realizing a microelectronic sensor device according to the present invention, a large area electronics (LAE) matrix approach, preferably an active matrix approach may be used in order to contact the heating elements and/or the sensor elements. The technique of LAE, and specifically active matrix technology using for example thin film transistors (TFTs) is applied for example in the production of flat panel displays such as LCDs, OLED and electrophoretic displays.

In the aforementioned embodiment, a line-at-a-time addressing approach may be used to address the heating elements by the control unit.

According to a further development of the microelectronic sensor device, the interface between the sample chamber and the heating and/or sensing array is chemically coated in a pattern that corresponds to the patterns of the heating elements and/or sensor elements, respectively. Thus the effect of these elements can be combined with chemical effects, for example with the immobilization of target molecules out of a sample solution at binding molecules which are attached to the interface.

The invention further relates to the use of the microelectronic sensor devices described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers/characters in the Figures refer to identical or similar components.

DESCRIPTION OF THE EMBODIMENT

Biochips for (bio)chemical analysis, such as molecular diagnostics, will become an important tool for a variety of medical, forensic and food applications. In general, biochips comprise a biosensor in most of which target molecules (e.g. proteins, DNA) are immobilized on biochemical surfaces with capturing molecules and subsequently detected using for instance optical, magnetic or electrical detection schemes. Examples of magnetic biochips are described in the WO 2003/054566, WO 2003/054523, WO 2005/010542 A2, WO 2005/010543 A1, and WO 2005/038911 A1, which are incorporated into the present application by reference.

One way to improve the specificity of a biosensor is by control of the temperature, which is often used during a hybridization assay to regulate stringency of the binding of a target biomolecule to a functionalized surface, e.g. the binding of a DNA strand to its complementary strand. A high stringency is required when for instance single point mutations are of interest. Besides being of high importance for hybridization assays, temperature control of a biosensor is needed in general. More generally, the ability to control temperature AND fluids on a biochip is essential. Besides general temperature or flow management, the ability to control fluid convection locally in combination with temperature control offers options to enhance dissolution of reagents, to enhance mixing of (bio)chemicals and to enhance temperature uniformity. In order to optimize the performance of a biosensor, it is therefore proposed here to incorporate a temperature processing array in a biosensor. Optionally this can further be combined with mixing or pumping elements.

A programmable temperature processing array or "heating array" can be used to either maintain a constant temperature across the entire sensor area, or alternatively to create a defined temperature profile if the bio sensor is also configured in the form of an array and different portions of the bio sensor operate optimally at different temperatures. In all cases, the heating array comprises a multiplicity of individually addressable and drivable heating elements, and may optionally comprise additional elements such as temperature sensors, mixing or pumping elements, and even the sensing element itself (e.g. a photosensor). Preferably, the heating array is realized using thin film electronics, and optionally the array may be realized in the form of a matrix array, especially an active matrix array. Whilst the invention is not limited to any particular type of biosensor, it can be advantageously applied to biosensors based upon optical (e.g. fluorescence), magnetic or electrical (e.g. capacitive, inductive . . . ) sensing principles. In the following, various designs of such biosensors will be described in more detail.

Figure 1:
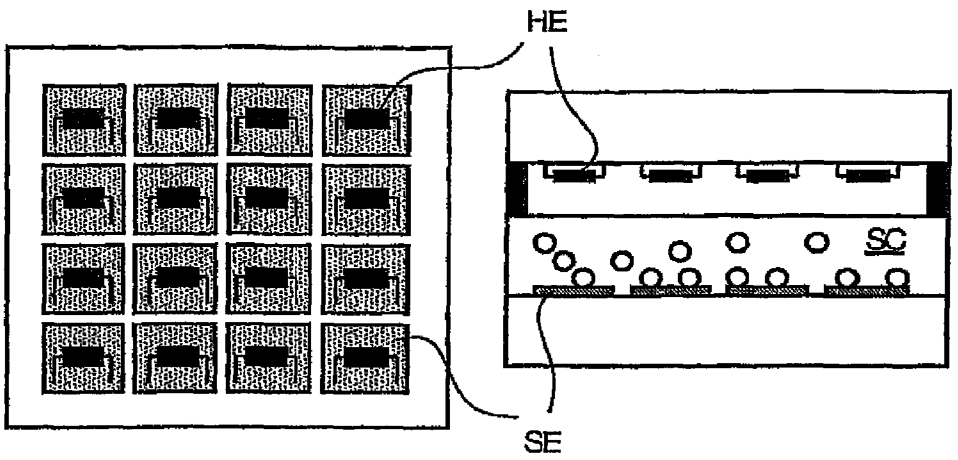
FIG. 1 shows a top view (left) and a cross section (right) of a biosensor with heating elements opposite to sensor elements.

FIG. 1 shows in a top view (left) and a cross section (right) how an array of heating elements HE may be added to an existing biosensor module, whereby it becomes possible to generate a pre-defined temperature profile across the array. In this embodiment, the biosensor module comprises a discrete biosensor device with an array of sensor elements SE and a discrete array of heating elements HE. The heating array of heating elements HE and the sensing array of sensor elements SE are located on opposite sides of a sample chamber SC which can take up a sample to be investigated. Each individual heating element HE may comprise any of the well known concepts for heat generation, for example a resistive strip, Peltier element, radio frequency heating element, radiative heating element (such as an Infra-red source or diode) etc. Each heating element is individually drivable, whereby a multiplicity of temperature profiles may be created.

Figure 2:
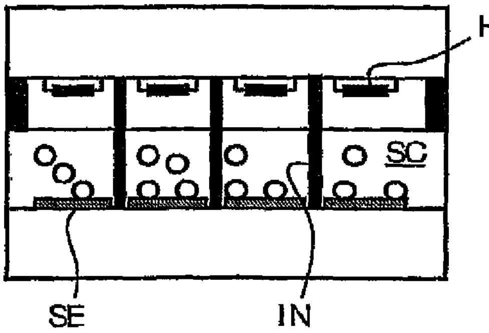
FIG. 2 shows a biosensor according to FIG. 1 with heat insulations.

There are several options for configuring the bio sensor module depending upon the required heat processing. In the embodiment shown in FIG. 2, the biosensor is configured in a series of compartments separated by heat isolation means IN (for example low heat conductivity materials like gasses such as air). In this manner, it is possible to simultaneously create compartments with different temperature (profiles), which may be particularly suitable for e.g. multi-parameter testing of DNA hybridization.

In another embodiment, the biosensor could be configured in larger compartments (or even a single compartment) with a multiplicity of heating elements in each large compartment. In this manner, it is possible to realize a well controlled temperature (profile) across the compartment, especially a constant temperature, which may be particularly suitable for e.g. analyzing biomolecules which are stable in a small temperature window (usually around 37° C.). In this embodiment the biosensor may further be provided with means to provide flow of the sample through the compartment, whereby the sample follows the local temperature profile. In this manner, it is possible to take the sample through a temperature cycle during or between the sensing operation.

Figure 3:
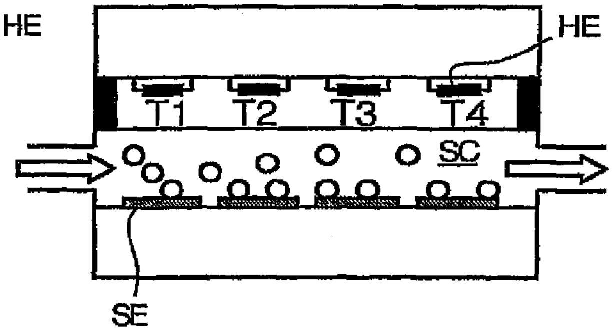
FIG. 3 shows a biosensor according to FIG. 1 with a flow chamber.

As shown in FIG. 3, the biosensors may optionally comprise flow channels, whereby the sample may be introduced into the analysis chamber(s) SC and subsequently removed after the analysis has been completed. In addition, the biosensor may comprise mechanical or electrical valves to contain the fluid in the biosensor or compartments of the biosensor for a certain period of time.

Figure 4:
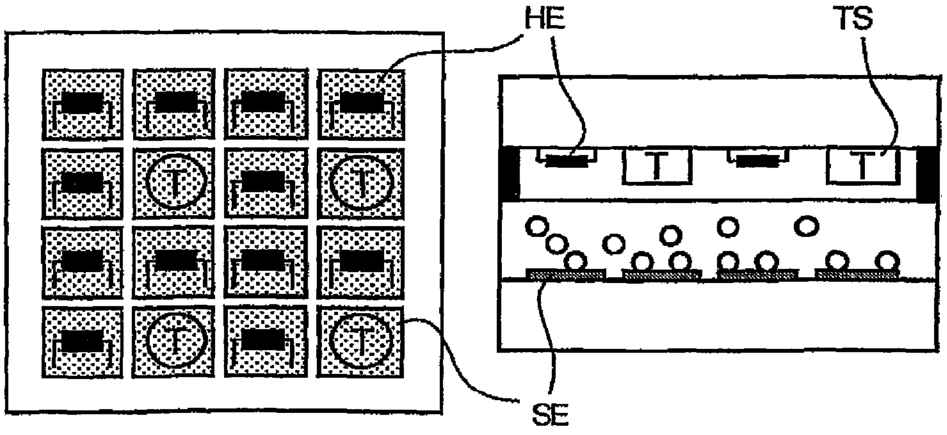
FIG. 4 shows a biosensor according to FIG. 1 with additional temperature sensors.

In the embodiment shown in FIG. 4, both an array of individually drivable heating elements HE and at least one temperature sensor TS are added to an existing biosensor module, whereby it becomes possible to generate and control a pre-defined temperature profile across the array. The temperature sensors TS may be used to prevent a temperature from extending beyond a given range, and may preferably be used to define and control the desired temperature profile. In a preferred embodiment, the temperature sensors TS could be integrated into the heating array, for example if this component were to be manufactured using large area thin film electronics technologies, such as low temperature poly-Si. In another embodiment, the array of heating elements HE and temperature sensor(s) TS may comprise a photosensor (e.g. photodiode) or discrete photosensor array. In that case the biosensing element in the biosensor may simply be a layer on which hybridization of specific (fluorescent) DNA strands occurs.

Figure 5:
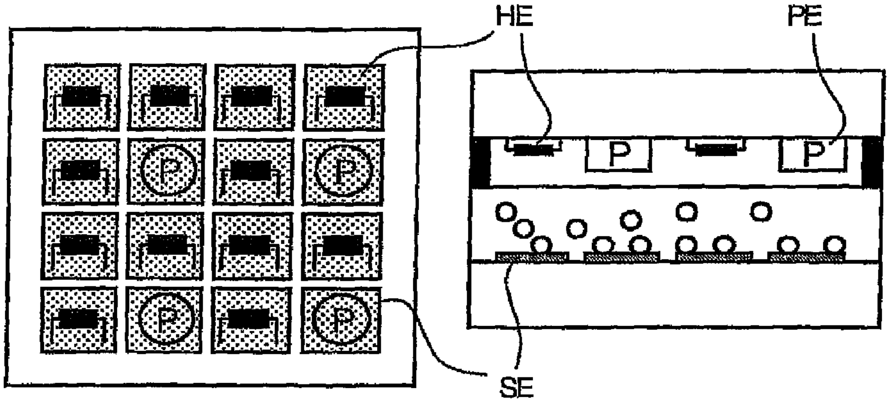
FIG. 5 shows a biosensor according to FIG. 1 with additional mixing/pumping elements.

In the embodiment shown in FIG. 5, both an array of individually drivable heating elements HE and at least one mixing or pumping element PE are added to an existing biosensor module, whereby it becomes possible to generate a more uniform temperature profile across the array. This is particularly advantageous if a constant temperature is required for the entire biosensor. Many types of mixing or pumping elements are known from the prior art, many of which are based upon electrical principles, e.g. electrophoretic, di-electrophoretic, electro-hydrodynamic, or electro-osmosis pumps. In a preferred embodiment, the mixing or pumping elements PE could be integrated into the heating element array, for example if this component were to be manufactured using large area thin film electronics technologies, such as low temperature poly-Si. As in the case of FIG. 4, the biosensor may further comprise a photosensor (e.g. photodiode) or discrete photosensor array.

Figure 6:
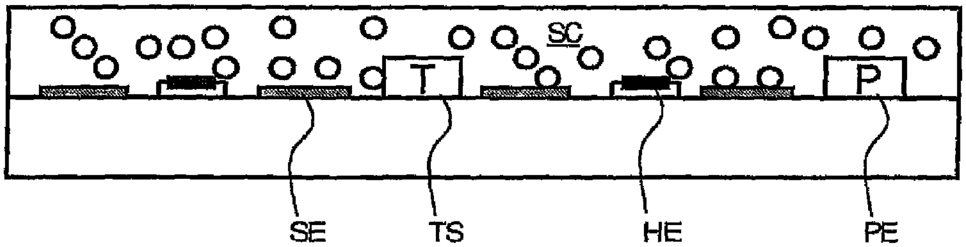
FIG. 6 shows a biosensor with an integrated array of heating elements, temperature sensors and mixing/pumping elements.

In the embodiment shown in FIG. 6, an array of individually drivable heating elements HE and/or temperature sensors TS and/or pumping or mixing elements PE is integrated with a biosensor, or an array of biosensors in a single component, whereby it becomes possible to generate and optionally control a pre-defined temperature profile across the array. Such a bio sensor or biosensor array may be manufactured using large area thin film electronics technologies, such as low temperature poly-Si. This may preferably be realized if the biosensor is based upon optical principles, as it is particularly suitable to fabricate photo-diodes in a large area electronics technology.

To enhance temperature control, in particular thermal cycling, means may be provided to cool a biosensors during operation, such as active cooling elements (e.g. thin film Peltier elements), thermal conductive layers in thermal contact with a heat sink or cold mass and a fan.

It should be noticed that the positioning of the heating elements HE is not limited to the embodiments shown in FIGS. 1-5, in which the heating elements are positioned on the opposite side of the sample chamber SC as the sensing elements SE. The heating elements may also be located at the same side of the fluid as the sensing elements, for example underneath, or on both sides of the chamber.

As was already pointed out, the array of heating elements may be realized in the form of a matrix device, preferably an active matrix device (alternatively being driven in a multiplexed manner). In an active matrix or a multiplexed device, it is possible to re-direct a driving signal from one driver to a multiplicity of heaters, without requiring that each heater is connected to the outside world by two contact terminals.

Figure 7:
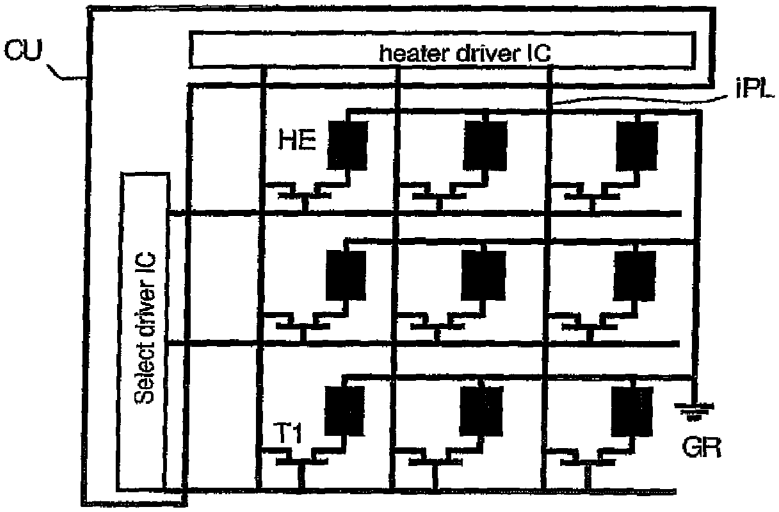
FIG. 7 shows schematically an active matrix heater array with the heater driver circuitry outside the array.

In the embodiment shown in FIG. 7, an active matrix is used as a distribution network to route the electrical signals required for the heaters from a central driver CU via individual power lines iPL to the heater elements HE. In this example, the heaters HE are provided as a regular array of identical units, whereby the heaters are connected to the driver CU via the transistors T1 of the active matrix. The gates of the transistors are connected to a select driver (which could be configured as a standard shift register gate driver as used for an Active Matrix Liquid Crystal Display (AMLCD)), whilst the source is connected to the heater driver, for example a set of voltage or current drivers. The operation of this array is as follows:

To activate a given heater element HE, the transistors T1 in the entire row of compartments incorporating the required heater are switched into the conducting state (by e.g. applying a positive voltage to the gates from the select driver).

The signal (voltage or current) on the individual power line iPL in the column where the heater is situated is set to its desired value. This signal is passed through the conducting TFT to the heater element, resulting in a local temperature increase.

The driving signal in all other columns is held at a voltage or current, which will not cause heating (this will typically be 0V or 0 A).

After the temperature increase has been realized, the transistors in the line are again set to the non-conducting state, preventing further heater activation.

As such, the matrix preferably operates using a "line-at-a-time" addressing principle, in contrast to the usual random access approach taken by CMOS based devices.

It is also possible to activate more than one heater HE in a given row simultaneously by applying a signal to more than one column in the array. It is possible to sequentially activate heaters in different rows by activating another line (using the gate driver) and applying a signal to one or more columns in the array.

Figure 8:
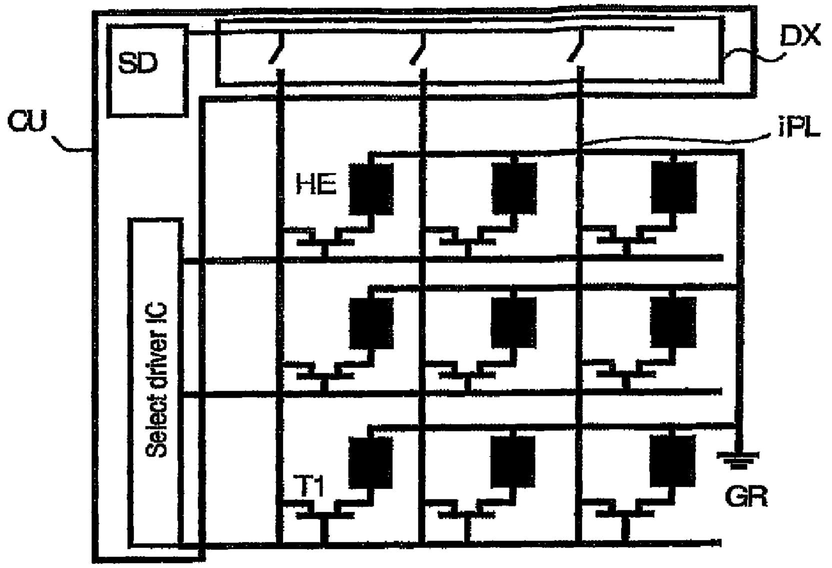
FIG. 8 shows a variant of FIG. 7 in which a single heater driver is connected via a de-multiplexer to the array of heating elements.

Whilst in the embodiment of FIG. 7 a driver is considered that is capable of providing (if required) individual signals to all columns of the array simultaneously, it would also be feasible to consider a more simple driver with a function of a de-multiplexer. This is shown in FIG. 8, wherein only a single output driver SD is required to generate the heating signal (e.g. a voltage or a current). The function of the de-multiplex circuit DX is simply to route the heater signal to one of the columns, whereby only the heater is activated in the selected row in that column. Alternatively, the de-multiplexer DX could be directly attached to a plurality of heating elements (corresponding to the case of only one row in FIG. 8). The function of the de-multiplex circuit is then simply to route the heater signal to one of its outputs, whereby only the desired heater is activated.

A problem with the simple approach of individually driving each heating element through two contact terminals is that an external driver is required to provide the electrical signals for each heater (i.e. a current source for a resistive heater). As a consequence, each driver can only activate a single heater at a time, which means that heaters attached to the same driver must be activated sequentially. This makes it difficult to maintain steady state temperature profiles. Furthermore, if a driving current is required, it is not always possible to bring the current from the driver to the heater without a loss of current, due to leakage effects.

Figure 9:
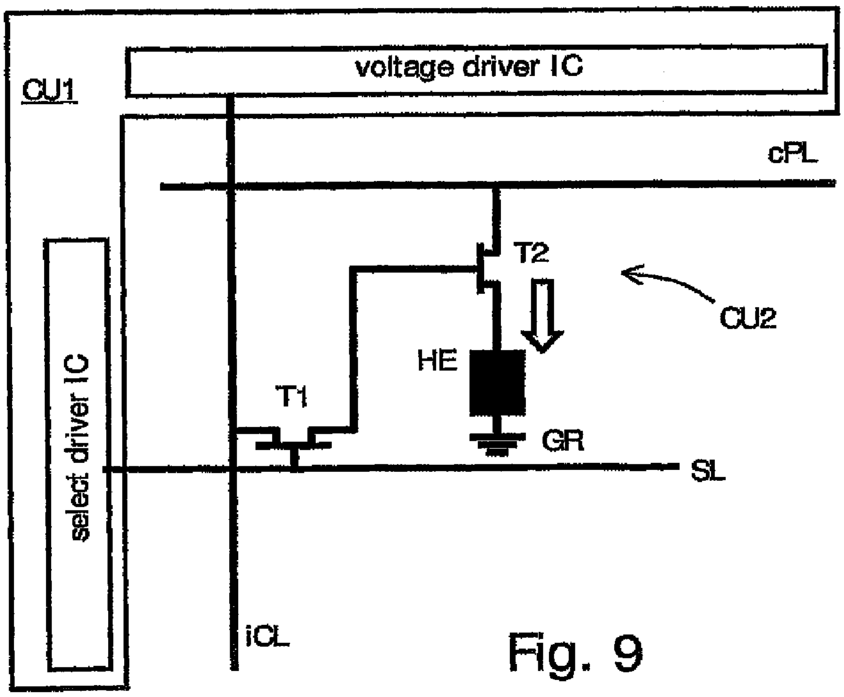
FIG. 9 shows schematically the circuit of an active matrix heater system with local driving units.

For this reason, it may be preferred to use the active matrix technology to create an integrated local heater driver per heating element. FIG. 9 illustrates such a local driver CU2 which forms one part of the control unit for the whole array; the other part CU1 of said control unit is located outside the array of heating elements HE (note that only one heating element HE of the whole array is shown in FIG. 9). Now every heating element HE comprises not only a select transistor T1, but also a local current source. Whilst there are many methods to realize such a local current source, the most simple embodiment requires the addition of just a second transistor T2, the current flowing through this transistor being defined by the voltage at the gate. Now, the programming of the heater current is simply to provide a specified voltage from the external voltage driver CU1 via individual control lines iCL and the select transistor T1 to the gate of the current source transistor T2, which then takes the required power from a common power line cPL.

Figure 10:
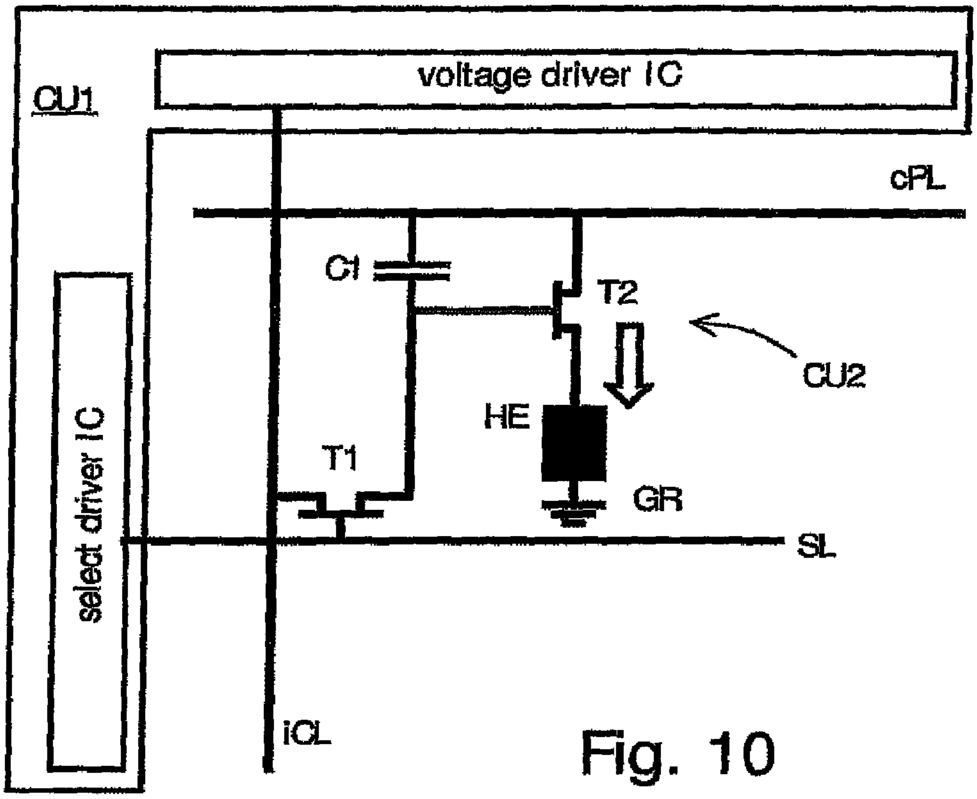
FIG. 10 shows the design of FIG. 9 with an additional memory element.

In a further embodiment shown in FIG. 10, the local driver CU2 can be provided with a local memory function, whereby it becomes possible to extend the drive signal beyond the time that the compartment is addressed. In many cases, the memory element could be a simple capacitor C1. For example, in the case of a current signal, the extra capacitor C1 is situated to store the voltage on the gate of the current source transistor T2 and maintain the heater current whilst e.g. another line of heater elements is being addressed. Adding the memory allows the heating signal to be applied for a longer period of time, whereby the temperature profile can be better controlled.

Whilst all the above embodiments consider the use of thin film electronics (and active matrix approaches) to activate the heating elements, in the most simple embodiment, the individual heating elements may all be individually driven, for example in the case of a resistive heating element by passing a defined current through the element via the two contact terminals. Whilst this is an effective solution for a relatively small number of heating elements, one problem with such an approach is that at least one additional contact terminal is required for each additional heating element which is to be individually driven. As a consequence, if a larger number of heating elements is required (to create more complex or more uniform temperature profiles), the number of contact terminals may become prohibitively large, making the device unacceptably large and cumbersome. It would also be possible to implement several of the embodiments using other active matrix thin film switching technologies such as diodes and MIM (metal-insulator-metal) devices.

Large area electronics, and specifically active matrix technology using for example Thin Film Transistors (TFT), is commonly used in the field of flat panel displays for the drive of many display effects e.g. LCD, OLED and Electrophoretic. In some embodiments of the present invention, it is proposed to use active matrix based heating arrays for biosensor application areas.

The problem however of a large area electronics based heating array in embodiments without a temperature sensing and control feature is that large area electronics suffers from non-uniformity in the performance of the active elements across the substrate. In the case of the preferred LTPS technology, it is known that both the mobility m and the threshold voltage $V_{thres}$ of transistors varies randomly from device to device (also for devices situated close to each other). If for example an LTPS transistor T2 is to be used as shown in FIG. 10 as a localized current source in an active matrix array, the most simple form of current source is the trans-conductance circuit with two transistors. In this case, the output current I of each current source is defined by $$I=\text{constant}\cdot m\cdot(V_{power}\cdot V-V_{thre})^2,$$

wherein $V_{power}$ is the power line voltage, V the programmed voltage to define the local temperature, and the constant is defined by the dimensions of the transistor. For this reason, any random variations of mobility m or threshold $V_{thre}$ will directly result in unwanted variations in the current provided and therefore to incorrect temperature values. This is a particular problem, as slightly incorrect temperatures can reduce the specificity of the sensing.

In the following, methods and circuits are therefore provided to realize a uniform temperature across an array of elements (cells) in an active matrix array with intrinsically variable transistor properties. Specifically, it is proposed to provide local current sources where either transistor variations in the mobility, the threshold voltage, or both are (partially) compensated. This results in a higher uniformity in the programmed current across the array. The approach is suited to large area glass substrate technologies such as Low Temperature Poly-Silicon (LTPS) rather than standard silicon CMOS because the areas involved are large which makes LTPS highly cost competitive.

Figure 11:
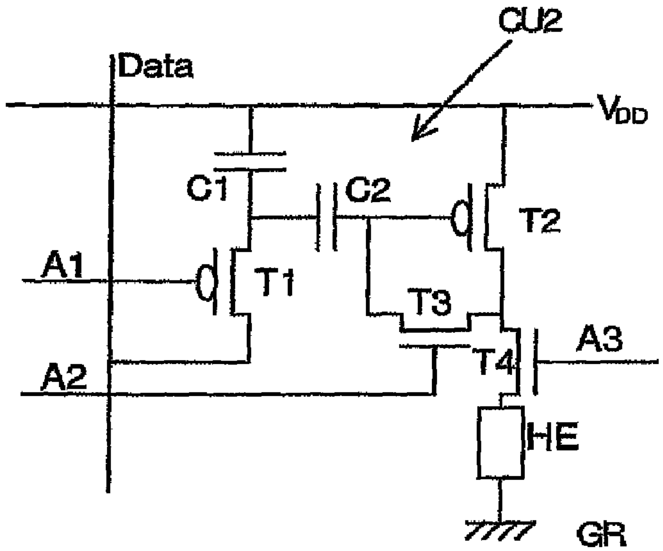
FIG. 11 shows a circuit of a local driving unit with means for compensating threshold voltage variations.

In a first embodiment, it is proposed to incorporate a threshold voltage compensating circuit into a localized current source for application in a programmable heating array. A wide variety of circuits for compensating for threshold voltage variations are available (e.g. R. M. A. Dawson and M. G. Kane, 'Pursuit of Active Matrix Light Emitting Diode Displays', 2001 SID conference proceeding 24.1, p. 372). For clarity this embodiment is illustrated using the local current source circuit shown in FIG. 11. This circuit operates by holding a reference voltage, e.g. $V_{DD}$, on the data line with the transistors T1 and T3, T4 pulsed that causes T2 to turn on. After the pulse, T2 charges a capacitor C2 to the threshold of T2. Then T3 is turned off storing the threshold on C2. Then the data voltage is applied and the capacitor C1 is charged to this voltage. The gate-source voltage of T2 is then the data voltage plus its threshold. Therefore the current (which is proportional to the gate-source voltage minus the threshold voltage squared) becomes independent of the threshold voltage of T2. Thus a uniform current can be applied to an array of heaters.

An advantage of this class of circuit is that the programming of the local current source can still be carried out with a voltage signal, as is standard in active matrix display applications. A disadvantage is that variations in the mobility of the TFT will still result in an incorrectly programmed temperature.

Figure 12:
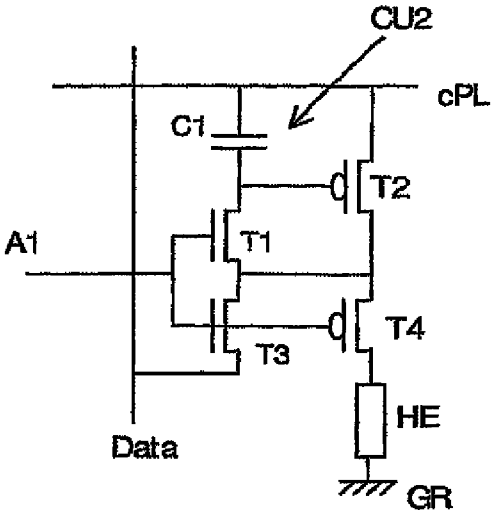
FIG. 12 shows a circuit of a local driving unit with means for compensating mobility and threshold voltage variations.

In order to address the latter point, it is further proposed to incorporate both a mobility and threshold voltage compensating circuit into a localized current source for application in a programmable heating array. A wide variety of circuits for compensating for both mobility and threshold voltage variations are available, especially based upon current mirror principles (e.g. A. Yumoto et al, 'Pixel-Driving Methods for Large-Sized Poly-Si AmOLED Displays', Asia Display IDW01, p. 1305). For clarity this embodiment is illustrated using the local current source circuit shown in FIG. 12. This circuit is programmed with a current when transistors T1 and T3 are on and T4 is off. This charges the capacitor C1 to a voltage sufficient to pass the programmed current through T2, which is operating in a diode configuration, with its gate attached to the drain via the conducting transistor T1. Then T1 and T3 are turned off to store the charge on C1, T2 now acts as a current source transistor and T4 is turned on to pass current to the heater. This is an example of a single transistor current mirror circuit, where the same transistor (T2) sequentially acts as both the programming part (in the diode configuration) and the driving part (in the current source configuration) of the current mirror. A compensation of both threshold and mobility variations of T2 is achieved so uniform currents can be delivered to an array of heaters.

An advantage of this class of circuit is that variations in the mobility of the TFT will also be compensated by the circuit. A disadvantage of this class of circuit is that the programming of the local current source can no longer be carried out with a voltage signal, as is standard in active matrix display applications.

Figure 13:
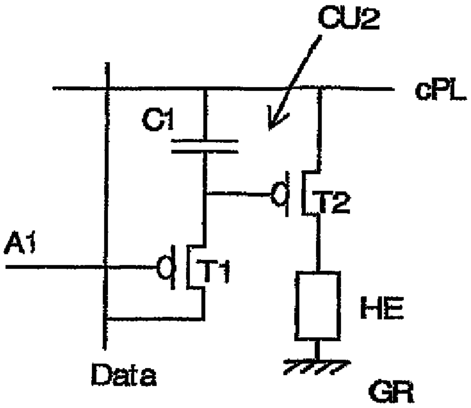
FIG. 13 shows a circuit of a local driving unit with a digital current source.

In another embodiment, it is proposed to incorporate a digital current driving circuit into a localized current source for application in a programmable heating array. In essence, the circuit directly connects the heating element HE to a power line voltage, whereby the characteristics of the TFT are less critical. The temperature is programmed by using a pulse width modulation (PWM) scheme. A wide variety of circuits for compensating for digital current driving are available (e.g. H. Kageyama et al., 'OLED Display using a 4 TFT pixel circuit with an innovative pixel driving scheme', 2002 SID conference proceeding 9.1, p. 96). For clarity this embodiment of the invention is illustrated using the local current source circuit shown in FIG. 13. In this case a voltage sufficient to bring T2 into its linear region is applied to the capacitor C1. Then the resistance of T2 is much less than that of the heater so very little voltage is dropped across T2 and therefore its variations in threshold and mobility are no longer important. Current and power are controlled by the length of time T2 is held in an ON stage. An advantage of this class of circuit is that the programming of the local current source can still be carried out with a voltage signal, as is standard in active matrix display applications.

In the above description of the drawings, reference is made to transistors in general. In practice, the temperature controlled cell-array is suited to be manufactured using Low Temperature Poly-Silicon (LTPS) Thin Film Transistors (TFT). Therefore, in a preferred embodiment, the transistors referred to above may be TFTs. In particular, the array may be manufactured on a large area glass substrate using LTPS technology, since LTPS is particularly cost effective when used for large areas.

Further, although the present invention has been described with regard to low temperature poly-Si (LTPS) based active matrix device, amorphous-Si thin film transistor (TFT), microcrystalline or nano-crystalline Si, high temperature poly SiTFT, other anorganic TFTs based upon e.g. CdSe, SnO or organic TFTs may be used as well. Similarly, MIM, i.e. metal-insulator-metal devices or diode devices, for example using the double diode with reset (D2R) active matrix addressing methods, as known in the art, may be used to develop the invention disclosed herein as well.

Finally it is pointed out that in the present application the term “comprising” does not exclude other elements or steps, that “a” or “an” does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A microelectronic sensor device, comprising:

a sample chamber defining a cavity;

a sensing array comprising a plurality of sensor elements arranged on one side of the sample chamber for sensing properties of a sample in the sample chamber;

a heating array comprising a plurality of heating elements arranged on another side of the sample chamber opposite the one side of the sample chamber on which the plurality of sensor elements are arranged, each heating element being configured to exchange heat with at least a sub-region within the cavity of the sample chamber when being driven with electrical energy; and a control unit for selectively driving the heating elements during or prior to the sensing of a sample in the sample chamber.

2. The microelectronic sensor device according to claim 1, wherein the control unit is adapted to drive the heating elements such that at least one of a desired spatial profile and a temporal temperature profile is achieved in the sample chamber.

3. The microelectronic sensor device according to claim 1, wherein the arrangements of elements in the sensing array and in the heating array are identical.

4. The microelectronic sensor device according to claim 1, wherein more than one heating element is associated to each sensor element.

5. The microelectronic sensor device according to claim 1, wherein the sensing array comprises at least one optical, magnetic, mechanical, acoustic, thermal or electrical sensor element.

6. The microelectronic sensor device according to claim 1, wherein the control unit is located outside the heating array and connected to the heating elements by power lines for selectively carrying electrical energy.

7. The microelectronic sensor device according to claim 6, wherein the control unit comprises a de-multiplexer for coupling it to the power lines.

8. A microelectronic sensor device, comprising:

a sample chamber;

a sensing array comprising a plurality of sensor elements for sensing properties of a sample in the sample chamber;

a heating array comprising a plurality of heating elements for exchanging heat with at least a sub-region of the sample chamber, corresponding to a sensor element of the plurality of sensor elements, when being driven with electrical energy; and a control unit for selectively driving the heating elements during or prior to the sensing of a sample in the sample chamber, wherein each heating element is associated with a local driving unit, wherein said driving units are located at and coupled to the heating elements.

9. The microelectronic sensor device according to claim 8, wherein all local driving units are coupled to a common power line and that all heating elements are coupled to another common power line.

10. The microelectronic sensor device according to claim 8, wherein a part of the control unit is located outside the heating array and connected to the local driving units via control lines for carrying control signals.

11. The microelectronic sensor device according to claim 10, wherein the control signals are pulse-width modulated.

12. The microelectronic sensor device according to claim 10, wherein the local driving units comprise a memory for storing the information of the control signals.

13. The microelectronic sensor device according to claim 8, wherein the local driving units comprise means for compensating variations of their individual characteristics.

14. The microelectronic sensor device according to claim 13, wherein at least one local driving unit comprises a transistor that produces fora given input voltage V an output current I according to the formula $$I=m\cdot(V-V\mathrm{thres})^2,$$

wherein mobility m and threshold voltage Vthres are individual characteristics of the transistor.

15. The microelectronic sensor device according to claim 14, wherein the local driving units each comprise a capacitor coupled to the control gate of the transistor and circuitry to charge the capacitor to a voltage that compensates Vthres or drives the transistor to produce a predetermined current I.

16. A microelectronic sensor device, comprising:

a sample chamber;

a sensing array comprising a plurality of sensor elements arranged within the sample chamber for sensing properties of a sample in the sample chamber;

a heating array comprising a plurality of heating elements and at least one pumping element for generating a more uniform temperature profile across the heating array, each of the plurality of heating elements being configured to exchange heat with at least a sub-region of the sample chamber corresponding to a sensor element of the plurality of sensor elements, when driven with electrical energy; and a control unit for selectively driving the heating elements during or prior to the sensing of a sample in the sample chamber.

17. The microelectronic sensor device according to claim 16, wherein the heating array further comprises at least one temperature sensor for sensing a temperature in the sample chamber.

18. The microelectronic sensor device according to claim 17, wherein the heating array and the sensing array are disposed on the same side of the sample chamber, wherein the arrays are merged in one layer.

19. The microelectronic sensor device according to claim 18, wherein the sensing array is disposed between the heating array and the sample chamber.

20. The microelectronic sensor device according to claim 16, wherein the heating array comprises two parts which are disposed on different sides of the sample chamber.

* * * * *